United States Patent [19]

Wehrli

[11] Patent Number: 4,635,378
[45] Date of Patent: Jan. 13, 1987

[54] APPARATUS FOR THE DEHUMIDIFYING MASONARY WORKS

[75] Inventor: Walter Wehrli, Diepoldsau, Switzerland

[73] Assignee: Terramundo Ltd., Jersey, Channel Islands

[21] Appl. No.: 796,024

[22] PCT Filed: May 23, 1984

[86] PCT No.: PCT/CH84/00082
§ 371 Date: Oct. 22, 1985
§ 102(e) Date: Oct. 22, 1985

[87] PCT Pub. No.: WO85/03732
PCT Pub. Date: Aug. 29, 1985

[30] Foreign Application Priority Data

Feb. 23, 1984 [EP] European Pat. Off. ........ 84101920.1

[51] Int. Cl.[4] .............................................. F26B 23/04
[52] U.S. Cl. .................................................. 34/1
[58] Field of Search ...................................... 34/1

[56] References Cited

U.S. PATENT DOCUMENTS 4,418,481 12/1983 Wehrli .

FOREIGN PATENT DOCUMENTS 1407151 9/1975 United Kingdom .

OTHER PUBLICATIONS

Deutsche Bauzeitschrift, Feb. and Jun. 80, No. 2, 6, Gutersloh (DE) H. W. Tenge: "Elektrophysikalische Verfahren zur Mauertrockenlegung Teil I, II," pp. 249-257, see pp. 927-950.

Primary Examiner—Albert J. Makay
Assistant Examiner—David W. Westphal
Attorney, Agent, or Firm—Cushman, Darby & Cushman

[57] ABSTRACT

Electrical conductors wound into coils (4, 5) are disposed in a housing (1). The axes of the coils (4, 5) run perpendicular to the base of the housing. Each coil (4, 5) is connected with a capacitor (2, 3) so that oscillatory circuits are formed. The longitudinal axes (10, 11) of the capacitors (2, 3) cross the coil axes at right angles and consequently run parallel to the base of the housing. In one (4) of the coils (4, 5) a permanent magnet (6) is inserted. Each coil has its own number of windings, its own outer diameter (15, 16), and advantageously its own inside diameter (18, 19). The oscillatory circuits are closed or opened by a switch (12). The oscillatory circuits are excited by the interfering fields present and generate in their turn a counter field. The process conforms essentially to the Lenz law of physics, according to which the reaction produced in the apparatus counteracts, and in the ideal case eliminates, the stimulating field action which produces it. As a result, the water in the capillary of the walling can no longer rise and the walling dries out in natural ways.

10 Claims, 4 Drawing Figures

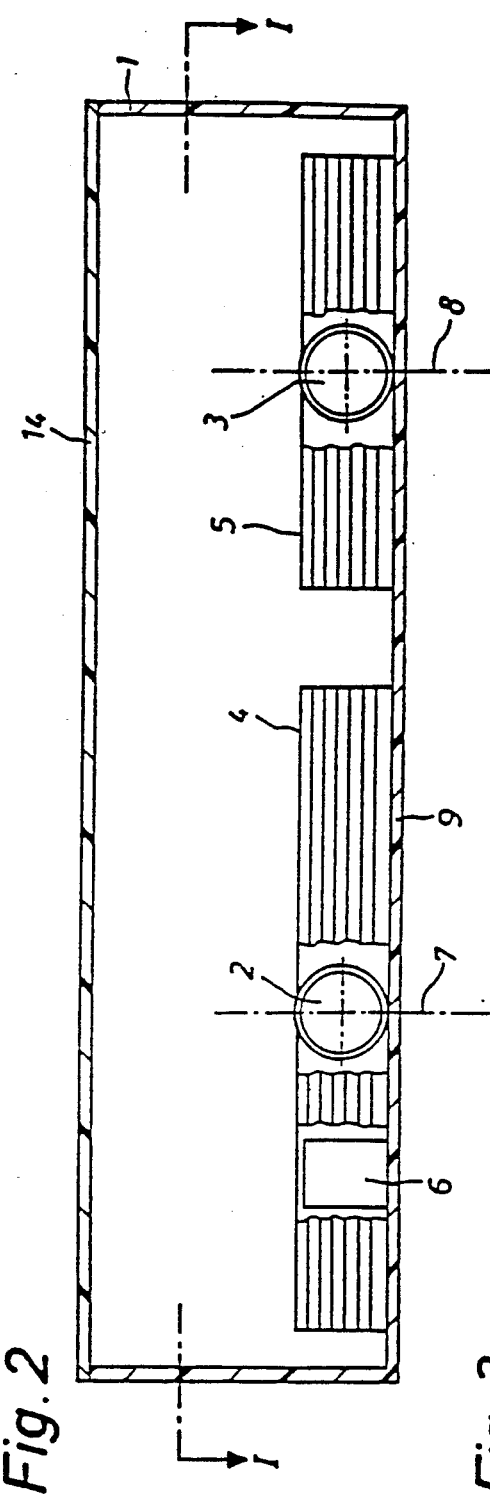
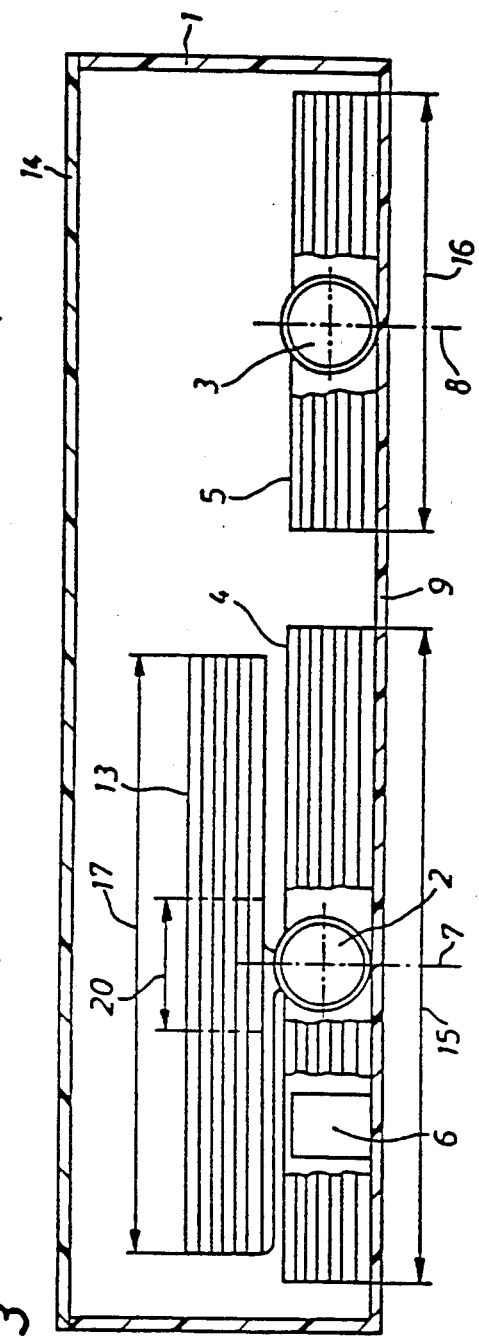
Fig. 2
Fig. 3

APPARATUS FOR THE DEHUMIDIFYING MASONARY WORKS

The invention relates to an apparatus for the dehumidifying masonary works in the case of dampness rising in the walling, which apparatus comprises capacitors and electrical conductors wound into coils, each of the two poles of a particular capacitor being connected to one end of a particular electrical conductor wound into a coil.

Considerable damage is caused in the walling of buildings by rising damp due to, for example, ground water, dammed-up water, percolating water or waters flowing underground.

Since all building materials are more or less porous, they take in the water because of their capillary action, with the result that the latter can rise within the walls.

Due to the osmotic pressure, the open circulation of water in a wet wall is conducted from the bottom to the top and at the latter point, by evaporation, to the outside. As a result of this transport of water an electric field is built up in the direction of the rising damp, and this field acts as a pump.

Damp walling leads not only to structural-engineering damage such as partial decay, crystalline blooms, encrustation etc., but can also lead to illnesses, e.g rheumatism, asthma, infectious diseases, etc., among people who reside in buildings with damp walling and in particular, a very uncomfortable room climate is also produced in such buildings.

The combating of rising damp in walls by inserting insulating layers is known. Various so-called electroosmoses methods are also known which generally require considerable structural measures, cannot be carried out at any point and without difficulty (drilling in house walls), and in many cases bear no relationship to the success achieved.

If the surfaces of two materials move past each other (friction), the two materials charge up electrically in the opposite sense at their boundary layers. If one material has a higher electrical conductivity under these circumstances than the other, then the first charges up positively and the second negatively.

If water moves in capillary walling, its electrical charge is opposite to that of the walling. An electrical potential difference, the ZETA POTENTIAL, arises between the two boundary layers. In these circumstances the water is drawn up in the capillaries by the opposite electrical charges and consequently wets wide areas of the walling. However, still other factors also have an influence, inter alia the salts dissolved in the water, the ionization of the air, etc. In the specialist world it is assumed that all these factors are influenced by the water conditions in the soil because underground flowing water is known to result in electric and magnetic fields which vary considerably in their strength, as a result of which the electrical conductivity of the water varies. In particular, these natural stimulated fields and increasingly also so-called civilization stimulated fields arising from technical installations (e.g high voltage lines laid in the ground etc.) act as further causes.

Depending on geophysical circumstances these stimulated fields extend over widely spread-out areas or stimulation zones. Now if such a zone extends through a building, the stimulated field becomes extremely inhomogeneous. In electrically insulating walling the field strength is greater than in the internal space it encloses, which fact results in the transport of the water molecules because of the strongly dielectric properties of water, either rising in the walling itself by capillary action or by diffusion to the walling from the air. This is the cause of the dampness formation.

As regards the physical nature of the stimulated fields, the specialist world, according to the latest knowledge, harbours the presumption that a stimulation zone represents a region in which strong activity of quiet atmospheric discharges prevails. These discharges have the character of charge fluctuations or of dipolar excited states, the description of which falls within the province of quantum physics. They appear to be related to the mechanism of the interval in atmospheric lightning discharges.

Now, apparatus in accordance with the preamble of patent claim 1 (U.S. Pat. No. 4,418,481) are known.

In these, 1-2 capacitors and 1-2 coils connected in each case therewith are present. In this connection the directions of the axes of the coils differ from one another, and these apparatus affect the electric earth field. It has emerged in practise that the rising of dampness in walling can be prevented by such apparatus. A precise, final technical explanation for this effect cannot yet be provided, but it is presumed that these apparatus respond to characteristics or to changes of the electric or magnetic earth field and in their turn form an influencing factor which counteracts the soil dampness rising in the walling. These known apparatus require no energy supply apart from that of the earth field. However, they exhibit an important defect in that they are strongly dependent in terms of their siting on local factors and usually take account only of the electric or only of the magnetic characteristics of the earth field, and as a result of this still too many failures or partial successes are achieved.

The invention is intended to provide a remedy in this connection. As it is characterised in the claims, the invention achieves the objective of providing an apparatus for the dehumidification of walling in which the above named factors are allowed for in a manner such that the apparatus functions satisfactorily in every case in which these conditions and factors are present and can be used without failures.

The advantages achieved by the invention are in essence to be seen in that the apparatus is absolutely insensitive to the precise orientation and height of its location in relation to the position of the maximum in the interfering field. It has been found that it was possible to use the apparatus satisfactorily and with success at the points at which the apparatus mentioned in the introduction were unsuccessful, which permits the use of the apparatus anywhere where perceptibly rising dampness is present and, in fact, independently of the constellation of the interfering field present, i.e. the interfering field may be of magnetic, electromagnetic or electrical nature or be formed as an interaction of these forces.

The invention is explained below by reference to several drawings representing embodiments:

FIG. 2 shows a section along the line II—II of FIG. 1 of the representation of a first embodiment;

FIG. 3 shows a representation similar to FIG. 2 of a second embodiment with three coils.

Figure 1:
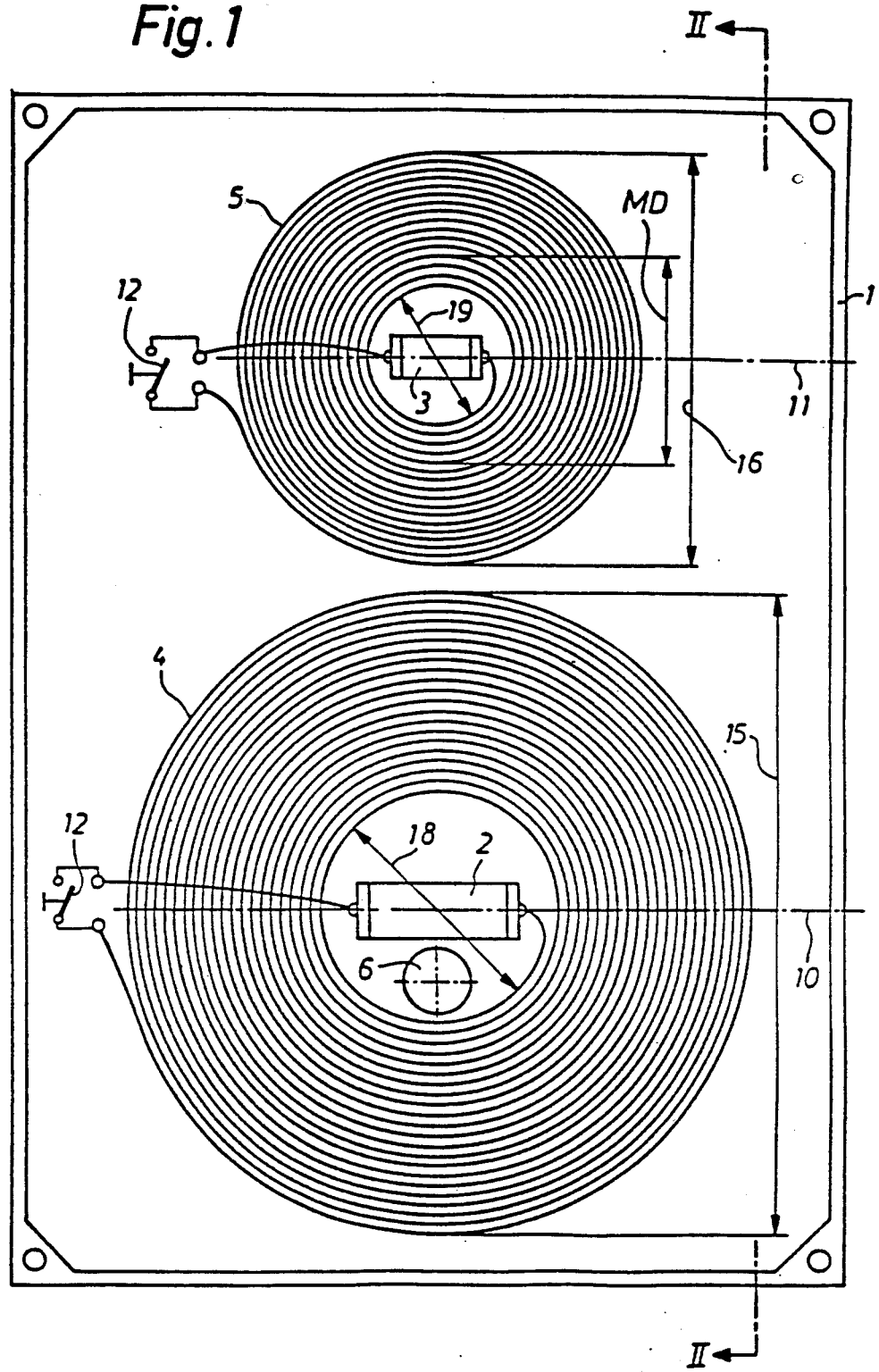
FIG. 1 shows a section along the line I—I of FIG. 2, a first embodiment being shown.

The apparatus comprises a housing of an electrically non-conducting material, which housing is denoted in all the figures by the reference number 1. According to the embodiment drawn in FIGS. 1 and 2, a first capacitor 2 and a second capacitor 3 are disposed in the housing 1. A first conductor wound into a first coil 4 and a second conductor wound into a second coil 5 are further present. At one end the first capacitor 2 is connected to one end of the first coil 4 and at the other end to the other end of the first coil 4, and at one end the second capacitor 3 is connected to one end of the second coil 5 and at the other end to the other end of the second coil 5. This results in circuits forming two oscillatory circuits. In the centre of the first coil 4 is disposed, in addition to the first capacitor 2, a permanent magnet 6. The centre axes 7, 8 of the coils 4, 5 run perpendicular to the base 9 of the housing 1 forming the supporting surface of the apparatus. The longitudinal axes 10, 11 of the capacitors 2, 3 cross the centre axes 7, 8 of the coils 4, 5 at right angles and consequently run parallel to the base 9 of the housing.

In order to be able to put the apparatus into operation or to take it out of operation, each oscillatory circuit is allocated a switch 12. Here a multiple switch may be present so that by means of operating, for example, a push button both oscillatory circuits can be closed or interrupted.

The apparatus shown in FIG. 3 differs from the version shown in FIGS. 1 and 2 in that a third coil 13 is present. This third coil 13 is connected to the first capacitor 2, and is therefore connected in parallel to the first coil 4. The axis of the third coil 13 coincides with the axis of the first coil 4.

The coils 2, 3 or 13 of the versions shown in FIGS. 1-3 are formed by wound conductors. Such a conductor may be insulated wire, e.g. a copoer leitz wire or an enamelled copper wire. The coils may also be partly formed by a printed circuit, a version being drawn in FIG. 4. All the coils 2, 3 and also 13, if a version with three coils is present, or only one coil may be formed as a plane printed circuit.

Figure 4:
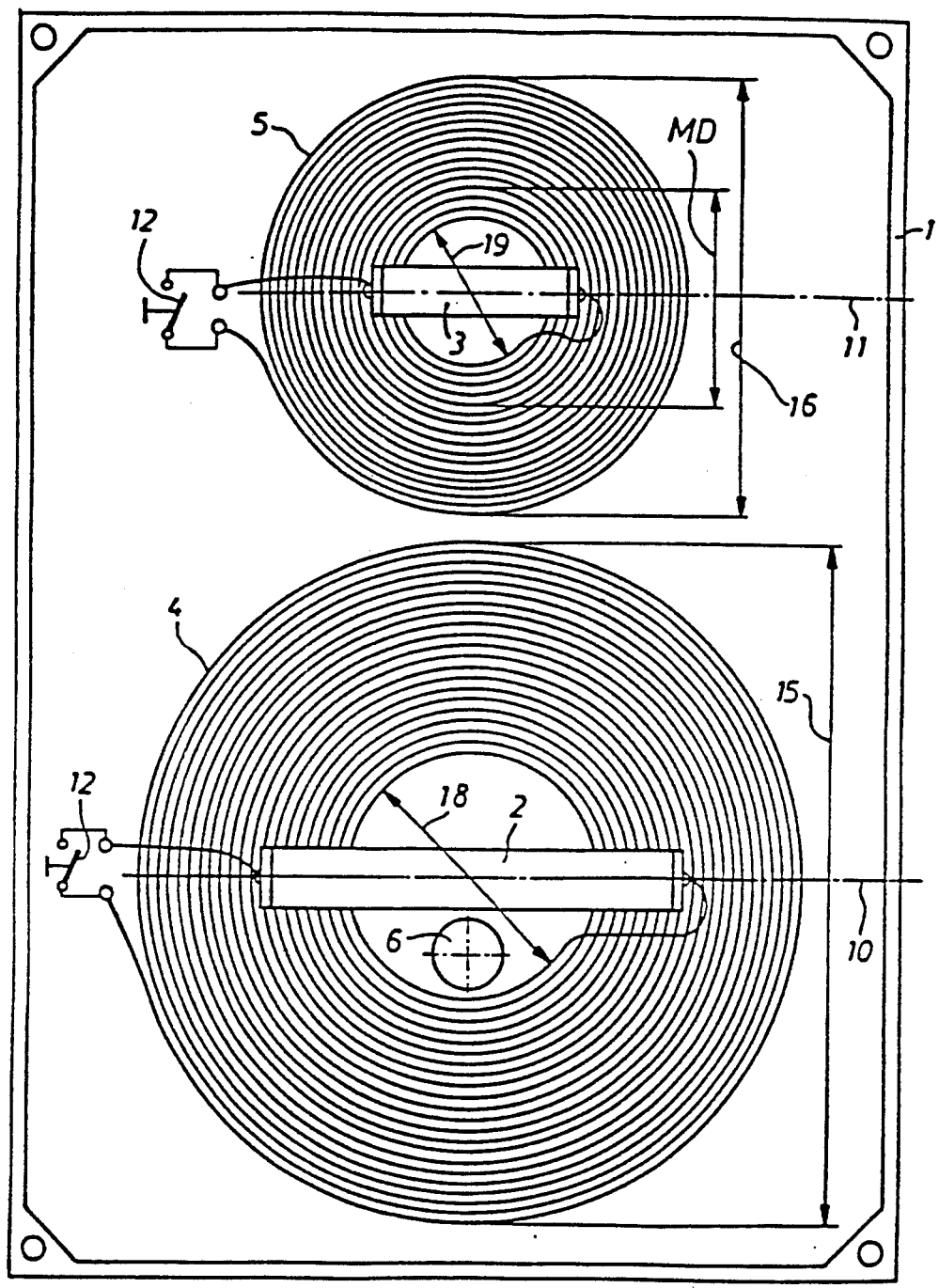
FIG. 4 shows a representation similar to FIG. 1 of a third embodiment with printed circuits for the coils.

In the version which is drawn in FIG. 4, the first coil 4 and the second coil 5 are formed as printed circuits. Again a permanent magnet is disposed in the first coil 4. Here again the longitudinal axes 10, 11 of the capacitors 2, 3 cross the centre axes of the coils 4, 5 at right angles. However, in the version shown in FIG. 4 the capacitors 2, 3 are to be considered as laid on the coils 4, 5 and not as surrounded by the coils 4, 5 as is the case in the versions according to FIGS. 1-3.

The housing 1 of all the versions consists of an electrically non-conducting material, in particular of plastic material in order to avoid screening of the earth field or of the interference fields acting on the apparatus. A cover 14 (see FIG. 3) seals off the housing 1, and this cover 14 may be provided with holes or slots to improve energy take-up or energy release.

The term "coil" is to be understood in the sense of an electrical inductance The particular capacitors 2, 3 form with the respective coils 4, 5, 13 a virtually damping-free electric parallel oscillatory circuit, which in essence complies with the Lenz law of physics, according to which the reaction produced in the apparatus counteracts the generating stimulated field action and in the ideal case eliminates it. The oscillatory frequency of the particular oscillatory circuits lies in general in the range of 10–44 kHz or 30–150 MHz. The size of the capacitors lies in general between 0.1 and 2.5 $\mu F$. The coils in each case comprise several windings, at least three windings.

The outside diameters 15, 16, 17 of the coils 4, 5, 13 (see FIGS. 1 and 3) are each of different size. In other versions the inside diameters 18, 19, 20 are in addition also of different size.

The dimension (outside diameter-inside diameter=MD) of the mean diameter MD (see the coil on the right in FIG. 1 (the smallest coil)) is at least 5 cm.

In order to prevent individual components in the housing 1 being able to move, for example if the apparatus is shaken, the housing 1 is advantageously filled with synthetic resin. In addition, the housing 1 and the lid 14 may themselves be manufactured from synthetic resin. The filling of the housing forms a reinforcement of the walls of the housing, the individual components being cast in synthetic resin.

The apparatus is also capable of functioning if the capacitor is removed by not more than the mean diameter MD of the particular coil from the centre of the latter.

To use the dehumidification apparatus the interfering field is first located at the point of use by means of an apparatus which indicates electromagnetic waves, or its field strength is determined. The apparatus must not then be sited directly on the stimulation strip of an interfering field or at the maximum field strength point, but next to such a point, and put into operation by completing the circuit by operating the switches or switch 12. The range of an apparatus may be up to several hundred meters.

The central arrangement of the capacitors relative to the coils allocated to them makes the apparatus more independent of its siting position and of its siting direction.

The oscillatory circuits disposed in the apparatus are excited by the energy of the interfering fields present and in their turn generate a counter field. As a result of the interference of the fields now present the latter are so strongly reduced, at least within the scope of the detectability at present known, that as a result a measurable reduction of the electrokinetically produced potential difference and the concentration of atmospheric ions occurs, which has the result that the water in the walling can no longer rise and the walling can dry out in natural ways.

I claim:

1. Apparatus for the dehumidifying masonary works which comprises capacitors and electrical conductors wound into coils, each of the two poles of a particular capacitor being connected to one end of a particular conductor wound into a coil, wherein at least a first and a second coil and at least a first and a second capacitor are present, the first capacitor is connected to the first coil and the second capacitor to the second coil, the axes of the coils run parallel to each other and the longitudinal axes of the capacitors cross the axes of the coils connected to them, and the coils are different in their outer diameter and their number of windings.

2. The apparatus of claim 1 wherein a permanent magnet is disposed in the centre of at least one of the coils.

3. The apparatus of claim 1 wherein the coils are different in their core diameter.

4. The apparatus of claim 1 wherein each coil comprises at least three windings.

5. The apparatus of claim 1 wherein the electrical conductors forming the coils are insulated.

6. The apparatus of claim 1 wherein the coils are formed of windings of insulated wire.

7. The apparatus of claim 1 wherein at least one coil is formed from a printed circuit.

8. The apparatus of claim 1 wherein the capacitors and coils are disposed in a housing of electrically nonconducting material, which housing has a support surface, and the longitudinal axis of each capacitor runs normally to the axis of the respective coil and parallel to the support surface.

9. The apparatus of claim 8 wherein the housing is completely filled with a synthetic resin which supports the coils and capacitors.

10. The apparatus of claim 1 wherein a third coil connected to the first capacitor and wired in parallel to the second is present, and the axes of the first and third coil coincide.

* * * * *